(12) United States Patent
Lomas et al.

(10) Patent No.: US 6,716,908 B2
(45) Date of Patent: Apr. 6, 2004

(54) ALKOXYSILYL FUNCTIONAL SILICONE BASED MATERIALS

(75) Inventors: Arnold Wade Lomas, Rhodes, MI (US); William James Schulz, Jr., Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/060,713

(22) Filed: Jan. 30, 2002

(65) Prior Publication Data

US 2003/0158326 A1 Aug. 21, 2003

(51) Int. Cl.[7] .................. C08L 83/05; C08L 83/06; C08L 83/07; A61K 7/00
(52) U.S. Cl. .................. 524/588; 524/267; 524/268; 524/861; 524/862; 524/863; 524/866; 424/401; 424/70.12
(58) Field of Search .................. 524/588, 267, 524/268, 862, 863, 866, 861; 525/478, 479, 101, 105; 424/401, 70.12

(56) References Cited

U.S. PATENT DOCUMENTS

| | | | |
|---|---|---|---|
| 4,714,739 A | * 12/1987 | Arkles | 525/92 G |
| 4,721,764 A | * 1/1988 | Fujiki et al. | 528/15 |
| 4,987,169 A | 1/1991 | Kuwata et al. | 524/267 |
| 5,420,222 A | * 5/1995 | Stepp et al. | 528/31 |
| 5,457,148 A | 10/1995 | Lucas | 524/731 |
| 5,470,923 A | 11/1995 | Krahnke et al. | 525/477 |
| 5,654,362 A | 8/1997 | Schulz, Jr. et al. | 524/862 |
| 5,665,804 A | * 9/1997 | Hill et al. | 524/268 |
| 5,760,116 A | 6/1998 | Kilgour et al. | 524/268 |
| 5,811,487 A | 9/1998 | Schulz, Jr. et al. | 524/862 |
| 5,840,800 A | * 11/1998 | Joffre et al. | 524/806 |
| 5,889,108 A | * 3/1999 | Zhang | 524/862 |
| 5,929,164 A | 7/1999 | Zhang | 524/862 |
| 5,969,035 A | * 10/1999 | Meinhardt et al. | 524/731 |
| 6,200,581 B1 | 3/2001 | Lin et al. | 424/401 |
| 6,291,563 B1 | * 9/2001 | Horne et al. | 524/267 |
| 6,331,604 B1 | 12/2001 | Wang et al. | 528/29 |

FOREIGN PATENT DOCUMENTS

| | | | | |
|---|---|---|---|---|
| EP | 1057476 A1 | 6/2000 | | A61K/7/48 |
| EP | 1132430 A1 | 12/2001 | | C08L/83/04 |

* cited by examiner

*Primary Examiner*—Jeffrey B. Robertson
(74) *Attorney, Agent, or Firm*—Alan Zombeck

(57) ABSTRACT

There are disclosed alkoxysilyl functional silicone based materials that are thermodynamically stable, methods for making them and their uses. The methods comprise cross-linking of reactants that are dispersed in a diluent.

25 Claims, No Drawings

ALKOXYSILYL FUNCTIONAL SILICONE BASED MATERIALS

FIELD OF THE INVENTION

This invention relates to alkoxysilyl functional silicone based materials, methods of making them and their uses. More particularly, the invention relates to thermodynamically stable materials comprising cross-linked siloxanes having alkoxysilyl functionality and a diluent, as well as to methods of making and the uses of such materials. The methods comprise cross-linking of reactants dispersed in a diluent.

BACKGROUND OF THE INVENTION

Thermodynamically stable silicone based materials comprising cross-linked siloxanes dispersed in a diluent are known in the art. One such material, made by polymerization of certain organohydrogenpolysiloxanes along with organopolysiloxanes having aliphatic unsaturated groups while in the presence of certain low viscosity silicones, is disclosed in U.S. Pat. No. 4,987,169 to Kuwata et al. Another such material is disclosed in U.S. Pat. No. 5,760,116 to Kilgour et al. In this last instance, certain alkenyl stopped polyorganosiloxanes are hydrosilylated with $\equiv$SiH containing "MQ" silicone resins in the presence of certain other silicones.

There are of course many variations possible in these materials and the synthesis of such materials. For example, the $\equiv$SiH groups and the aliphatic unsaturation may be on either or even both hydrosilylation reactants, as may other functionality. Sometimes, this allows for the synthesis of the same or a very similar type material using very different reactants in the same type of reaction. For example, what could be called a variant of Kilgour is seen in EP 1 057 476 by Fry, wherein the unsaturation appears in the resin and the $\equiv$SiH functionality appears in the other hydrosilylation reactant.

As with many other silicone based materials, it is has been found that inclusion of certain functional groups in the thermodynamically stable types discussed here can impart or enhance desirable properties. One example, where the polyether functionality is used, can be seen in U.S. Pat. No. 5,811,487 to Schulz et al. Here, the polyether functionality was introduced by hydrosilylation prior to cross-linking. It may also be of note that the cross linker may be purely hydrocarbon as was the case in this last mentioned material.

There is a continual need for new functionalized silicone based materials. New alkoxysilyl functional silicone based materials would be of great interest as they often have superior durability and/or enhance durability in formulations containing them.

Certain alkoxysilyl functional silicones and their formulations are well known in the art, notably as caulks, sealants and pressure sensitive adhesives. Such materials and methods for making them are exemplified by those disclosed in U.S. Pat. No. 5,470,923 to Krahnke et al. and U.S. Pat. No. 5,457,148 to Lucas. These prior art materials are not, however, thermodynamically stable (at least as defined herein below) and are usually much too effective in enhancing durability to be suitable for many applications in the personal care industry. In addition, use of these materials does not typically result in desirable aesthetics in many of the applications for which compositions of the present invention are designed.

The present invention provides thermodynamically stable, alkoxysilyl functional silicone based materials capable of suitably enhancing durability of personal care products while providing desirable aesthetics.

SUMMARY OF THE INVENTION

It is an object of the present invention to provide novel, thermodynamically stable, alkoxysilyl functional silicone based materials. In this regard, the invention relates to thermodynamically stable materials comprising:
(A) a cross-linked siloxane comprising:
alkoxysilyl functionality, $-X-SiR^4{}_n(OR^5)_{3-n}$, and
cross-links, $-E^1-Y-E^2-$, with each end of such cross-links bonded to a silicon,
wherein,
X is a divalent group that is a hydrocarbon, a siloxane or some combination of these,
$R^4$ and $R^5$ are independently monovalent hydrocarbon groups,
$E^1$ and $E^2$ are independently $-CH_2CH_2-$ or $-CH=CH-$,
Y is a divalent group that is a hydrocarbon, a siloxane or some combination of these, and
n is 0 to 2;
and
(B) a diluent.

It is a further object of this invention to provide methods of making thermodynamically stable, alkoxysilyl functional silicone based materials. Thus, the invention further relates to a method of making a thermodynamically stable material, the method comprising cross-linking, in the presence of a hydrosilylation catalyst,
(1) an $\equiv$SiH functional siloxane,
(2) an alpha, omega diene, diyne or ene-yne (as defined later herein),
with the provisos
that at least one of (1) and (2) has alkoxysilyl functionality, $-X-SiR^4{}_n(OR^5)_{3-n}$,
where,
X is a divalent group that is a hydrocarbon, a siloxane or some combination of these,
$R^4$ and $R^5$ are independently monovalent hydrocarbon groups and
n is 0 to 2,
that (1) and (2) are dispersed in a diluent, and
that the weight ratio of (1)+(2)+ the product of the cross-linking of (1) and (2):diluent is 1:100 to 10:1.

The invention also relates to materials preparable, as well as those prepared by, the methods according to the present invention. In addition, the invention relates to personal care products containing the compositions of the present invention.

DETAILED DESCRIPTION OF THE INVENTION

The compositions of the present invention include thermodynamically stable materials comprising:
(A) a cross-linked siloxane comprising:
alkoxysilyl functionality, $-X-SiR^4{}_n(OR^5)_{3-n}$, and
cross-links, $-E^1-Y-E^2-$, with each end of such cross-links (meaning at $E^1$ and $E^2$ on the side opposite from Y as shown here) bonded to a silicon,
wherein,
X is a divalent group that is a hydrocarbon (especially one having 2 to 12 carbons), a siloxane or some combination of these, R$^4$ and R$^5$ are independently monovalent hydrocarbon groups (especially those having 1 to 30 carbons), E$^1$ and E$^2$ are independently —CH$_2$CH$_2$— or —CH=CH—, Y is a divalent group that is a hydrocarbon (especially one having 1 to 30 carbons), a siloxane or some combination of these and is 0 to 2;

and (B) a diluent.

(These compositions will be denoted hereinafter for convenience as those "explicitly defined".)

In the context of this disclosure and the claims that follow, thermodynamically stable refers to a material comprising a cross-linked polymer and a diluent that is homogeneous immediately after shearing and remains as such for at least 72 hours after being sheared, where homogeneous refers to something with a constant bulk viscosity (the type measured in units of cP, mPa s or equivalent units such as in a Brookfield device and sometimes referred to as absolute viscosity as opposed to kinematic viscosity) throughout a given sample within +/−10 percent.

One method for determining such thermodynamic stability is the Dow Corning Corporation Thermodynamic Stability test (hereinafter, the "DCCTS test"), wherein a sample of material is first sheared then visually inspected for homogeneity. If the sheared material is found to be visually homogenous, then viscosity is measured using a statistically significant number of random samples of the sheared material taken immediately after the visual inspection and again 72 hours later. The material is considered thermodynamically stable if all viscosity measurements (for accuracy's sake, these are taken as, respectively, the mean of several measurements at the same point) from the initial sampling and the sampling 72 hours later are within +/−10 percent of their respective means.

Alkoxysilyl functionality is normally associated with the backbone portion of the cross-linked siloxane, but it may occur in the cross links or even in both the backbone and cross links at the same time and this disclosure and claims that follow should be interpreted to include these variations whenever possible, unless otherwise indicated. Of course in polymers made from similarly sized backbone components and cross linkers, it can be a little difficult to determine which is which in the final polymer, but this distinction usually makes no difference except for convenience in discussion.

It is possible a particular polymer molecule may have several different types of backbone elements as well as several different cross linker elements. The alkoxysilyl functionality can be distributed among these in any fashion as long as present somewhere in the polymer molecule.

Representative examples of alkoxysilyl functionality include groups such as CH$_2$CH$_2$Si(OR$^5$)$_3$, where R$^5$ is methyl, ethyl, isopropyl, phenyl, benzyl or combinations of these.

For simplicity, throughout this disclosure and claims that follow, the term siloxane should be understood in its broad sense so as to include organo and other substituted siloxanes, polysiloxanes, and organo and other substituted polysiloxanes. This is of course understood to be distinct from a hydrocarbon. Reference to a combination of a siloxane and a hydrocarbon, should be taken to mean a hydrocarbon bridging two or more siloxanes or a siloxane bridging two or more hydrocarbons or something made up of two or more of these; such combination could be termed a siloxane of course, but not a hydrocarbon.

It should be understood that throughout this disclosure and the claims that follow that ranges should be interpreted as specifically including and disclosing all subranges and individual values subsumed. For example, a range of 1 to 10 would include and disclose a range of 2–5 and a range of 6–8, as well as 1.72, 7.76 and 9.9, among other subranges and individual vales in the overall range. Of course, this understanding would apply correspondingly to other types of ranges, such as "C1 to C5 hydrocarbons" and "a value of at least 80 percent".

In this disclosure and the claims that follow, it should be understood that a diluent may be a single compound or a mixture of compounds. Suitable examples include silicones such as siloxanes, both linear and cyclic (other than the corresponding cross-linked siloxane chosen for (A)), organic oils, organic solvents and mixtures of these. Some more specific examples of diluents may be found in U.S. Pat. No. 6,200,581, which is hereby incorporated by reference for this purpose. Non-reactive or relatively non-reactive diluents are preferred. For purposes here, non-reactive is used in reference to the associated cross-linking reaction and used relative to the (other) reactants therein. A relatively non-reactive diluent would be less than one tenth as reactive with the other reactants as the others are with each other in the associated cross-linking reaction.

As has previously been mentioned, alkoxysilyl functionality acts to increase durability (substantivity) in silicone based materials containing it, but there are aesthetic issues with the prior art materials. Surprisingly, in the compositions according to the present invention, durability rapidly reaches a suitable range for most personal care applications with increasing alkoxysilyl content without the negative effect on aesthetics of the prior art materials. The compositions according to the present invention are also good film formers with excellent aesthetics and have good bonding characteristics further enhancing their desirability in personal care applications. Given the wide variety of diluents that may be employed in making these compositions, compatibility is rarely ever an issue.

One embodiment of the explicitly defined compositions of the present invention that is of great interest is the material wherein:

(A) is a cross-linked alkoxysilyl functional siloxane of average formula:

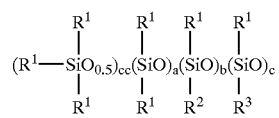

where,

R$^1$ is a monovalent hydrocarbon group (preferably one having 1 to 30 carbons or 1 to 12 carbons and especially alkyl, aryl, alkaryl, aralkyl, or combinations thereof with a very preferred choice being methyl);

R$^2$ is —(CH$_2$)$_d$SiR$^4{}_n$(OR$^5$)$_{3-n}$;

R$^3$ is —E$^1$—Y—E$^2$—R$^9$ or a siloxane containing (somewhere in its structure as pendant, internal, terminal or otherwise) —E$^1$—Y—E$^2$—R$^9$ with E$^1$ in this last mentioned siloxane bonded to silicon as well as to Y, R$^4$ and R$^5$ are independently monovalent hydrocarbon groups (preferably one having 1 to 30 carbons or 1 to 12 carbons and especially alkyl, aryl, alkaryl, aralkyl, or combinations thereof, with very preferred choices for R$^5$ including methyl, ethyl, isopropyl, phenyl or benzyl);

$E^1$ and $E^2$ are independently —$CH_2CH_2$— or —CH=CH—;

Y is a divalent group that is a hydrocarbon (especially one having 1 to 30 carbons), a siloxane or some combination of these with one preferred Y being,

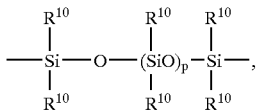

where $R^{10}$ is a monovalent hydrocarbon group (especially methyl) and p is 0 to 20,000 (especially 0 to 500);

$R^9$ is

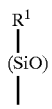

(which can be thought of as the "other side" of the cross link);

a is 0–100,000,000;

b is 1–50,000,000;

c is 1–10,000,000;

$4<=cc<=2c+2$ (here and throughout cc represents a single value, not a product of c and c);

d is 2–12;

n is 0–2.

In reference to polymer formulae in this disclosure and the claims that follow, "average" should be understood to be a number or molar average, unless otherwise indicated. Also in this disclosure and the claims that follow, it should be understood that that formulae given for polymers (such as the one for the cross linked siloxane given just above) should be regarded as only semi-structural such that the subscripts for various subunits indicate merely the number present in the molecule as opposed to the particular position shown. Further, no stereospecificity is intended by what is shown in such formulae.

A very suitable diluent (B) for this last embodiment is a siloxane other than that chosen for (A) or a mixture of siloxanes not containing that chosen for (A).

One preferred weight ratio range for (A):(B) for this embodiment is 1:100 to 10:1. This ratio is also generally applicable to other compositions of the present invention.

Another embodiment of the explicitly defined compositions of the present invention that is of great interest is the material wherein:

(A) is a cross-linked alkoxysilyl functional siloxane of average formula:

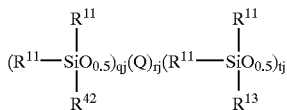

where, $R^{11}$ is a monovalent hydrocarbon group (preferably having 1 to 40 or 1 to 20 carbons);

$R^{42}$ is a monovalent hydrocarbon group (preferably having 1 to 40 or 1 to 20 carbons) or —$(CH_2)_d SiR^4{}_n (OR^5)_{3-n}$, with the proviso that $R^{42}$ is at least in part —$(CH_2)_d SiR^4{}_n (OR^5)_{3-n}$;

$R^{13}$ is —$E^1$—$R^{16}$—Y—$R^{17}$—$E^2$—$R^{19}$, or a siloxane containing —$E^1$—$R^{16}$—Y—$R^{17}$—$E^2$—$R^{19}$ with $E^1$ in this last mentioned siloxane bonded to silicon and $R^{16}$;

Q is on average at least 80 mole percent ($SiO_2$) with the balance made up of one or more other types of siloxane units;

$R^4$ and $R^5$ are independently monovalent hydrocarbon groups (preferably having 1 to 30 or 1 to 12 carbons and especially alkyl, aryl, alkaryl, aralkyl or combinations thereof with $R^5$ especially methyl, ethyl, isopropyl, phenyl or benzyl);

$E^1$ and $E^2$ are independently —$CH_2CH_2$— or —CH=CH—;

$R^{16}$ and $R^{17}$ are independently divalent hydrocarbon groups (especially having 1 to 8 carbons) or nullities;

Y is a divalent group that is a hydrocarbon, a siloxane or a combination of these, with one preference being:

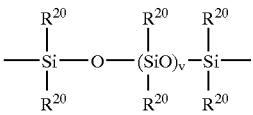

where, $R^{20}$ is a monovalent hydrocarbon group having from 1 to 40 carbons and v is 0 to 20,000 (especially 100 to 5,000 or 500 to 5,000);

$R^{19}$ is

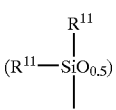

(which can be thought of as the "other side" of the cross link);

j is 1 to 100;

q is 1 to 500,000;

r is 1 to 1,000,000;

t is 1 to 100,000;

d is 2 to 12; and n is 0 to 2, with the proviso that q+t:r is 0.5 to 4.0 (here and throughout qj, rj and tj represent products of q and j, r and j, and t and j, respectively).

As is indicated here for $R^{42}$, and should be taken as the case for other R and similarly designated groups throughout this disclosure and the claims that follow, variation is possible for a particular R or similarly designated group even within the same molecule. Of course, variation is limited to within the overall definition of the group. For example, if $R^{100}$ is defined as a monovalent hydrocarbon group, then $R^{100}$ might represent methyl groups in some and ethyl groups at other of the various positions it shows up in a particular molecule.

It should be understood that in this disclosure and the claims that follow that "siloxane units" refers to one of the silicon based building blocks found in siloxanes and polysiloxanes. These are commonly referred to in the art as "M" ($\equiv SiO_{0.5}$), "D" ($=SiO$), "T" (—$SiO_{1.5}$) and "Q" ($SiO_2$) units, as well as functionalized and/or substituted versions of these. One particular "T" type siloxane unit of interest in the immediately preceding embodiment of the compositions of the present invention is "T—OH" (HO—$SiO_{1.5}$).

In the context of a divalent R or similarly designated divalent group, it should be understood that "nullity" means "nothing there". For example, in —X—Y—Z—, if —Y— is a nullity, then —X—Y—Z— is the same as —X—Z—.

The cross-linked component of the compositions of the present invention is often made up of enormous polymer molecules. Sometimes it may be convenient to describe this component and the overall composition in terms of subunits. This concept is utilized in describing yet another embodiment of the explicitly defined compositions of the present invention wherein:

(A) is a cross-linked alkoxysilyl functional siloxane comprising subunits of formula

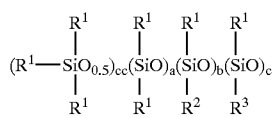

where, $R^1$ is a monovalent hydrocarbon group (preferably having 1 to 30 or 1 to 12 carbons and especially alkyl, aryl, alkaryl, aralkyl or combinations thereof);

$R^2$ is —$(CH_2)_d SiR^4_n (OR^5)_{3-n}$;

$R^3$ is —$E^1$—Y—$E^2$—$R^9$ or a siloxane containing (somewhere in its structure as pendant, internal, terminal or otherwise) —$E^1$—Y—$E^2$—$R^9$ with $E^1$ in this last mentioned siloxane bonded to silicon as well as to Y, $R^4$ and $R^5$ are independently monovalent hydrocarbon groups (preferably having 1 to 30 or 1 to 12 carbons and especially alkyl, aryl, alkaryl, aralkyl or combinations thereof with $R^5$ especially methyl, ethyl, isopropyl, phenyl or benzyl);

$E^1$ and $E^2$ are independently —$CH_2CH_2$— or —CH=CH—;

Y is a divalent group that is a hydrocarbon, a siloxane or some combination of these;

$R^9$ is

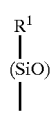

(which may be thought of as the "other side" of the cross-link);

a is 0–1,000;
b is 1–500;
c is 1–100;
4<=cc<=2c+2;
d is 2–12; and
n is 0–2.

As in the polymer formulae of this disclosure and the claims that follow, those given for polymer subunits as here should be regarded as only semi-structural such that the subscripts for various units indicate merely the number present in the subunit as opposed to the particular position shown. Further, no stereospecificity is intended by what is shown in such formulae.

Another embodiment of the explicitly defined compositions of the present invention also with component (A) expressed in terms of subunits is one wherein:

(A) is a cross-linked alkoxysilyl functional siloxane comprising subunits of formula:

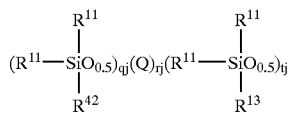

where, $R^{11}$ is a monovalent hydrocarbon group (preferably having 1 to 40 or 1 to 20 carbons);

$R^{42}$ is a monovalent hydrocarbon group (preferably having 1 to 40 or 1 to 20 carbons) or —$(CH_2)_d SiR^4_n (OR^5)_{3-n}$, with the proviso that $R^{42}$ is at least in part —$(CH_2)_d SiR^4_n (OR^5)_{3-n}$;

$R^{13}$ is —$E^1$—$R^{16}$—Y—$R^{17}$—$E^2$—$R^{19}$, or a siloxane containing —$E^1$—$R^{16}$—Y—$R^{17}$—$E^2$—$R^{19}$ with $E^1$ in this last mentioned siloxane bonded to silicon and $R^{16}$;

Q is on average at least 80 mole percent ($SiO_2$) with the balance made up of one or more other types of siloxane units (as defined previously, including "T—OH");

$R^4$ and $R^5$ are independently monovalent hydrocarbon groups (preferably having 1 to 30 or 1 to 12 carbons and especially alkyl, aryl, alkaryl, aralkyl or combinations thereof with $R^5$ especially methyl, ethyl, isopropyl, phenyl or benzyl);

$E^1$ and $E^2$ are independently —$CH_2CH_2$— or —CH=CH—;

$R^{16}$ and $R^{17}$ are independently divalent hydrocarbon groups or nullities;

Y is a divalent group that is a hydrocarbon, a siloxane or a combination of these $R^{19}$ is

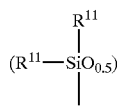

(which can be thought of as the "other side" of the cross-link);

j is 1 to 100;
q is 1 to 500;
r is 1 to 1000;
t is 1 to 100;
d is 2 to 12; and
n is 0 to 2, with the proviso that
q+t:r is 0.5 to 4.0.

The present invention also relates to methods of making the compositions previously described and compositions related to them as described below that are also part of the invention. Thus, the methods of the present invention are for making thermodynamically stable materials, the methods comprising cross-linking, in the presence of a hydrosilylation catalyst:

(1) an ≡SiH functional siloxane and
(2) an alpha, omega diene, diyne or ene-yne (as defined herein below), with the provisos that at least one of (1) and (2) (very often (1)) has alkoxysilyl functionality, —X—$SiR^4_n (OR^5)_{3-n}$, where, X is a divalent group that is a hydrocarbon (preferably having 2 to 12 carbons), a siloxane or some combination of these, $R^4$ and $R^5$ are independently monovalent hydrocarbon groups and n is 0 to 2, that (1) and (2) are dispersed in a diluent (which may be a single compound or mixture as previously discussed), and that the weight ratio of (1)+(2)+ the product of the cross-linking of (1) and (2):diluent is 1:100 to 10:1.

Any hydrosilylation catalyst, of which many are well known in the art, may be utilized, such as those based on noble metals like platinum, notably Karstedt's catalyst. Karstedt's catalyst, a platinum divinyl tetramethyl disiloxane based composition, is described extensively in the art such as in U.S. Pat. No. 5,654,362. Homogeneous, heterogeneous or mixtures of homogeneous and heterogeneous form catalysts may be employed.

It may be advantageous in some instances to control reaction using a catalyst quencher. Quenching of this type is presented in U.S. Pat. No. 5,929,164. It is not essential that a quencher be used in the methods of the present invention, but one may be employed if desired.

In this disclosure and the claims that follow, especially in the context of the methods of the present invention, ≡SiH functionality should be understood in its broad sense. That is it may be pendant, internal, terminal or otherwise or some combination of these. It may be of note (and is shown in the examples) that alkoxysilyl functionality is often introduced in a hydrosilylation step prior to the cross-linking step shown above with only a portion of the available ≡SiH consumed in this prior step.

Especially in the context of the methods of the present invention, but also generally in this disclosure and the claims that follow, "alpha, omega diene, diyne or ene-yne" should be understood to refer to compounds wherein there is at least a pair of terminal aliphatic unsaturated groups with some separation. Structurally, this would (in the "alpha, omega diyne" case) look something like HC≡C—L—C≡CH, where L could be for example hydrocarbon, siloxane or some combination of these. The unsaturation could be at an end or pendant if part of a polymer or resin molecule.

An embodiment of the methods of the present invention of great interest is one where, (1) is an alkoxysilyl functional siloxane of average formula:

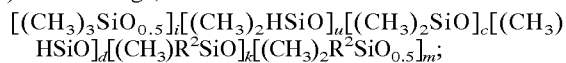

where, $R^1$ is a monovalent hydrocarbon group (preferably having 1 to 30 or 1 to 12 carbons and especially alkyl, aryl, alkaryl, aralkyl or combinations thereof);

$R^2$ is —$(CH_2)_d SiR^4_n(OR^5)_{3-n}$;

$R^4$ and $R^5$ are independently monovalent hydrocarbon groups (preferably having 1 to 30 or 1 to 12 carbons and especially alkyl, aryl, alkaryl, aralkyl or combinations thereof with $R^5$ especially methyl, ethyl, isopropyl, phenyl or benzyl);

a is 0–1,000;

b is 1–500;

c is 1–100;

2<=cc<=2c+2;

d is 2–12; and n is 0–2;

(2) is $E^3$—Y—$E^4$ or a siloxane containing (somewhere in its structure as pendant, internal, terminal or otherwise) $E^3$—Y—$E^4$, where $E^3$ and $E^4$ are independently $CH_2$=CH— or CH≡C—; and Y is a multivalent group (divalent or higher valency) that is a hydrocarbon, a siloxane or some combination of these.

Another embodiment of the methods of the present invention of great interest is one where, (1) is on average, $[(CH_3)_3SiO_{0.5}]_i[(CH_3)_2HSiO]_u[(CH_3)_2SiO]_c[(CH_3)HSiO]_d[(CH_3)R^2SiO]_k[(CH_3)_2R^2SiO_{0.5}]_m$;

$R^2$ is —$(CH_2)_p SiR^4_n(OR^5)_{3-n}$;

$R^4$ and $R^5$ are independently monovalent hydrocarbon groups, (preferably having 1 to 30 or 1 to 12 carbons and especially alkyl, aryl, alkaryl, aralkyl or combinations thereof with $R^5$ especially methyl, ethyl, isopropyl, phenyl or benzyl);

i is 0 to 2;

u is 0 to 2;

i+u+m=2;

c is 0 to 20,000 (preferably 100 to 5000 or 500 to 5000);

d is 0 to 2000 (preferably 0 to 200);

u+d>=2;

k is 0 to 2000 (preferably 0 to 500);

m is 0 to 2;

k+m>=1;

p is 2 to 12;

n is 0 to 2; and (2) is on average $[(CH_2=CH)(CH_3)_2SiO_{0.5}]_e[(CH_3)_3SiO_{0.5}]_f[(CH_3)_2SiO]_g[(CH_2=CH)(CH_3)SiO]_h$;

e is 0 to 2;

f is 0 to 2;

e+f=2;

g is 0 to 20,000 (preferably 0 to 500);

h is 0 to 1000 (preferably 0 to 50);

e+h>=2

Still another embodiment of the methods of the present invention of great interest is one where, (1) is on average

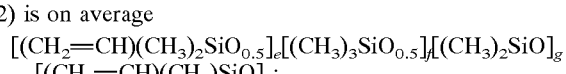

where, $R^{11}$ is a monovalent hydrocarbon group (preferably having 1 to 40 or 1 to 20 carbons);

$R^{42}$ is a monovalent hydrocarbon group (preferably having 1 to 40 or 1 to 20 carbons) or —$(CH_2)_q SiR^4_n(OR^5)_{3-n}$, with the proviso that $R^{42}$ is at least in part —$(CH_2)_q SiR^4_n(OR^5)_{3-n}$;

Q is on average at least 80 mole percent ($SiO_2$) with the balance made up of one or more other types of siloxane units (as defined previously including "T—OH");

$R^4$ and $R^5$ are independently monovalent hydrocarbon groups (preferably having 1 to 30 or 1 to 12 carbons and especially alkyl, aryl, alkaryl, aralkyl or combinations thereof with $R^5$ especially methyl, ethyl, isopropyl, phenyl or benzyl);

j is 1 to 100;

q is 1 to 500;

r is 1 to 1000;

t is 1 to 100;

d is 2 to 12;

n is 0 to 2;

q+t:r is 0.5 to 4; and (2) is on average

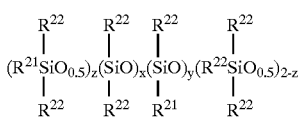

where x is 0 to 20,000 (preferably 100 to 20,000 or 100 to 5000);

y is 0 to 2000, z is 0 to 2,

2<=z+y<=2000, $R^{21}$ is a monovalent, terminally aliphatic unsaturated hydrocarbon having from two to twelve carbons, and $R^{22}$ is a monovalent hydrocarbon having one to forty carbons.

Yet another embodiment of the methods of the present invention of great interest is one where, (1) is an ≡Si—H functional polyorganosiloxane and (2) is a polyorganosiloxane resin having alpha-omega diene, diyne or ene-yne (as defined previously) functionality.

An important refinement of this last embodiment is one where at least 80 mole percent of subunits in the polyorganosiloxane resin of (2) are ($SiO_2$) and (($R^i$)$_3SiO_{0.5}$), where $R^i$ is a monovalent hydrocarbon group, the ratio in (2) of siloxane units other than $SiO_2$ to $SiO_2$ units there is 0.5 to 4.0, and X in the alkoxysilyl functionality is a hydrocarbon.

It is sometimes convenient to express a composition (implicitly) in terms of a method to make it. This invention includes compositions that are the product of (made by, prepared by, etc.) any of the methods of the present invention.

The compositions of the present invention are often clear and nearly solid materials. These may be diluted with a suitable diluent to form pastes, gels or fluids as required.

The invention also includes compositions, such as personal care products, made from any of the compositions of the present invention previously described herein. This would include hair, skin and underarm care products. Some more specific examples would be conditioners, moisturizers, body washes, cosmetic foundations, blushes, lipsticks, eye liners, mascaras, eye shadows, antiperspirants and deodorants. Other examples of products that can be made from the compositions of the present invention are the same as can be made from the materials disclosed in U.S. Pat. No. 6,200,581, which is hereby incorporated by reference for these examples.

In this disclosure and the claims that follow, it should be understood that in the context of a chemical formula that Me stands for methyl. Further, compositions expressed in percent should be taken as being in weight percent, unless otherwise indicated.

Titles in the examples that follow are merely descriptive and should not be viewed as limiting in any way.

EXAMPLES

Examples 1–3
Synthesis of Certain Alkoxysilyl Functional Silicones

Into an Esco® EL 1 processor (mixer) is loaded 400.00 g (less the amount used to dilute the hexadiene added below—see note in Table 1) of decamethylcyclopentasiloxane (hereinafter "$D_5$") and a measured amount (see Table 1) of a silicon hydride containing siloxane having an average structure, ($Me_3SiO$)($Me_2SiO$)$_{93}$($MeHSiO$)$_6$($SiMe_3$), (hereinafter, ≡SiH). The temperature controller is set to 70° C., and the wiper blades are adjusted to a setting of 15 and the homogenizer to a setting of 10.

When the temperature reaches 70° C., 0.2 ml of Karstedt's catalyst with a Pt content of 0.52 weight percent is added, immediately followed by the required (see Table 1) vinyl (trimethoxy)silane (hereinafter, "VTMS"). The temperature is then increased to 75° C. and held for 30 minutes with continuing agitation.

Next, an additional 0.8 ml of the same Karstedt's catalyst is added, immediately followed by the subsurface addition of a measured amount (see Table 1) of 1,5-hexadiene (hereinafter, "HD") solution. The resulting exotherm (5–10° C.) indicates that the reaction is proceeding as desired. The system is then held at 75° C. for 3 hours with the wiper blade at a setting of 15 and the homogenizer at a setting of 20.

At the end of the three hour period, 3.50 g of a vinylsiloxane oligomer with the average structure [($CH_2$=CH)$SiMe_2O$]($Me_2SiO$)$_8$ [$SiMe_2$(CH=$CH_2$)] (hereinafter, "DVS") is added and mixed in at temperature for an additional 10 minutes. (This material is added as a catalyst quencher, and although a potential cross-linker, it is unlikely to form many cross-links given the proportions of the reactants used here. It is not essential that a quencher be used in synthesis of the compositions according to the present invention.) The mixture is then cooled by setting the temperature controller on the mixer to 20° C. while continuing the shear.

After a cooling period of 30 minutes, the scraper is set to 20 and the homogenizer to 25 and 269.00 g of additional $D_5$ is added in order to achieve 13% solids by weight in the mixture.

TABLE 1

Amounts Used in Examples 1–3 and Resulting Functionality

| Example | ≡SiH (g) | HD[a] (g) | VTMS (g) | % Alkoxysilyl[b] |
|---|---|---|---|---|
| 1 | 96.21 | 3.27 | 0.51 | 4.5 |
| 2 | 95.86 | 3.12 | 1.02 | 9.0 |
| 3 | 93.77 | 2.22 | 4.01 | 36.0 |

[a]this amount of HD is delivered as a 10 weight % solution in a portion of the original 400 g charge of $D_5$.
[b]Expressed as a mole percentage of total SiH functionality (groups) converted to alkoxysilyl functionality (groups).

Extent and relative completion of the cross-linking reactions and molecular weight of the final polymers are determined, at least qualitatively, by measuring viscosity at intervals after the periods outlined above.

Example 4
Demonstration of Thermodynamic Stability (DCCTS Test)

As has been previously discussed, in the context of this disclosure and the claims that follow, thermodynamically stable refers to a material comprising a cross-linked polymer and a diluent that is homogeneous immediately after shearing and remains as such for at least 72 hours after being sheared, where homogeneous refers to something with a constant bulk viscosity (the type measured in units of cP, mPa s or equivalent units such as in a Brookfield device and sometimes referred to as absolute viscosity as opposed to kinematic viscosity) throughout a given sample within +/−10 percent.

One method for determining such thermodynamic stability is the DCCTS test, wherein a sample of material is first sheared then visually inspected for homogeneity. If the sheared material is found to be visually homogenous, then viscosity is measured using a statistically significant number of random samples of the sheared material taken immediately after the visual inspection and again 72 hours later. The material is considered thermodynamically stable if all viscosity measurements (for accuracy's sake, these are taken as, respectively, the mean of several measurements at the same point) from the initial sampling and the sampling 72 hours later are within +/−10 percent of their respective means.

In this example, the DCCTS test was run on the product of Example 1. Prior to the taking of the first set of viscosity readings, the sample was sheared for 4 minutes at medium-low speed (setting 2–4) in a Waring commercial blender, model 7012S, using an SS110 pulverizer cup. After shearing, the sample was transferred to a 4 fluid ounce (118.3 ml) jar, then deaired for 5 minutes. The sample was cooled for 15 minutes prior to measuring viscosity to compensate for heat build up during shear. Visual inspection indicated that the sheared sample was homogeneous.

Viscosity was measured in 5 different areas of the sheared sample, using the heliopath feature on the Brookfield RVDV-II+ viscometer employed. With the T-spindles, the level was set at 0.25 in (0.64 cm) into the material, the viscometer was turned on, and the readings were allowed to level off (after about 1 to 2 minutes). The heliopath feature was then switched on, which allowed the spindle to travel downward while rotating. This ensures that the spindle traveled through untouched material as it went through the material. The spindle traveled a pre-set distance (1 inch or 2.54 cm) and then traveled upward. The measurements were taken automatically (spindle 94 at 2.5 rpm), at 15 second intervals, and only on the first downward and upward travel. The automatic reading was turned on after the heliopath feature was turned on (to avoid a reading right at the top where the spindle has been rotating for several turns), so some measured areas have 1 less reading than others due to difficulties in technician coordinating the speed of the test. Areas were not re-measured once disturbed. All areas had 7–9 readings at 15 second intervals. The mean and standard deviation was measured for each area and reported in units of viscosity. The mean and standard deviation of the entire population was then calculated. Viscosities were again determined at 72 hours. Results are shown in Table 2 below. The viscosities for each reading were within 10 percent of the overall mean for both the initial and 72 hours tests indicating the material was thermodynamically stable.

TABLE 2

Results from DCCTS Test

| Reading | Mean (cP = mPa s) | Standard Deviation (cP = mPa s) |
|---|---|---|
| | Initial | |
| 1 | 243,000 | 6020 |
| 2 | 239,000 | 8320 |
| 3 | 241,000 | 6480 |
| 4 | 258,000 | 20,300 |
| 5 | 261,000 | 33,100 |

TABLE 2-continued

Results from DCCTS Test

| Reading | Mean (cP = mPa s) | Standard Deviation (cP = mPa s) |
|---|---|---|
| Overall population = 40 | 248,400 | 19,600 |
| | After 72 hours | |
| 1 | 284,000 | 16,500 |
| 2 | 297,000 | 17,300 |
| 3 | 285,000 | 11,900 |
| 4 | 297,000 | 25,970 |
| 5 | 285,000 | 14,800 |
| Overall population = 38 | 289,700 | 18,200 |

Comparative Example 1
Synthesis of a Silicone Without Alkoxysilyl Functionality

A silicone without alkoxysilyl functionality was made following the procedure of Examples 1–3 using 96.57 g ≡SiH and 3.43 g HD, but no VTMS.

Examples 5–7
Formulation of Liquid Cosmetic Foundations

Liquid cosmetic foundations were prepared containing the materials as shown in Table 3.

TABLE 3

Liquid Cosmetic Foundation Formulations

| Ingredient | Parts by weight | Source |
|---|---|---|
| Phase A | | |
| Pigment Blend | 15.0 | Cardre ® Caprylylsilane-Treated Iron Oxide & Titanium Dioxide |
| Cyclomethicone | 21.5 | Dow Corning ® 245 Fluid |
| Cyclomethicone & Dimethicone Copolyol | 7.5 | Dow Corning ® 3225C Formulation Aid |
| Alkoxysilyl Functional Silicone | 10.0 | Product of Examples 1, 2 and 3 for Examples 5, 6 and 7, respectively |
| Phase B | | |
| Water | 54.8 | deionized |
| Sodium Chloride | 1.0 | Fisher ® |
| Polysorbate 20 | 0.2 | Tween ® 20 by ICI |

The procedure used for making the foundation formulations is as follows. Combine the ingredients in Phase A, using the product of Examples 1, 2 and 3, respectively for Examples 5, 6 and 7 for the alkoxysilyl functional silicone, then mix until uniform using a dual blade, turbulent mixing action and continue mixing to keep uniform. Next, combine the ingredients in Phase B and mix until uniform. Increase the mixing speed of Phase A to a tip velocity of 900 ft/min (274.32 m/min) and very slowly add Phase B. This addition should be over about 10 minutes. Continue mixing for an additional 10 minutes.

Comparative Example 2
Formulation of Another Liquid Cosmetic Foundation

A liquid cosmetic foundation was prepared using the method in Examples 5–7, except that the product of Comparative Example 1 was used in place of the alkoxysilyl functional silicone.

Example 8 and Comparative Example 3
Abrasion Testing of Cosmetic Foundations

The cosmetic foundations prepared in Examples 5–7 and Comparative Example 2, as well as a control and an industry standard, were tested using a modified Gardner Abrasion Tester. The test involves applying the foundations to collagen substrates that had been previously held in a 98% relative humidity chamber for at least 8 hours. The foundation is then tested for durability. The tester slides a soft sided Velcro® patch against the test surface. Changes in the surface are monitored with a spectrophotometer. Results are reported as a % color change.

Modified Gardner Abrasion Test

1. Cut collagen substrates into 3.5 in×3 in (8.89 cm×7.62 cm) pieces, place one on each of 3 in×2.5 in (7.62 cm×6.35 cm) polycarbonate blocks and put into a humidity chamber overnight. This chamber must be at a constant 98% relative humidity level.
2. Remove collagen and block from humidity chamber. Secure collagen to block with Scotch tape taking care not to place any on the top of the block's surface.
3. Using a four decimal place balance, tare the balance and weigh the block and collagen. Record weight.
4. Add approximately 1 gram of foundation to the collagen, beading it across the top of the block.
5. Using a clean #8 Meyer rod, coat the collagen with the foundation by placing the rod on the bead of foundation and spreading it downward to the bottom of the block. The final coating weight should be approximately 0.2 grams. This operation may need to be repeated to obtain the proper coating weight. Remove any material from the sides of the block. Record sample weight.
6. Allow the coated collagen sample to dry. Record the drying time. Drying times vary with different samples. The entire sample must be free from any wetness or tack before testing.
7. Before sample testing, standardization must be performed per manufacturer's instructions on the Hunter Lab Color Quest 45/0 spectrophotometer employed.
8. Setup will include verifying that the standard software (Universal, version 3.1) on the spectrophotometer will take three readings, fifteen seconds apart. This can be done in the Read menu under "timed read method".
9. To test the sample, Place the sample face down on the light source with the side that is labeled "Top" on the side away from the user.
10. To begin testing, click on the "Read Sample" icon located in the toolbar. After three readings have been taken, it will ask the user to accept the data. Click on accept, type in a brief identification name for the sample and that the reading is at time zero. Press Enter.
11. Remove the block and place it face-up on the Gardner Abrasion Tester (model KAG-8100 by BYK Gardner) with the side marked "Top" up, securing the block to the abrasion tester using Velcro attached to the track of the tester. The track was modified using polycarbonate to allow the sled to slide across the entire surface of the track and over the test block located in the center of the track at the same surface level as the track. The sled insults the test sample by rubbing across the test surface with a strip of soft Velcro adhered to the bottom side of the sled. Start the sled on the left side of the block with the Velcro strips facing downward. Depress the "power" button and press the "run" button. Allow the insult block to move across the sample and back twice. Depress the "power" button when the insulting block is on its way back during the second trip. Using two insults is the recommended amount for this test.
12. Remove the block from the abrasion tester and test the sample on the spectrophotometer as in part 8 above.
13. Repeat the "insult and test" procedure for a total of 20 times.

TABLE 4

Test Results from Modified Gardner Abrasion Testing

| Sample | % Color Loss after 20 Insults | % Color Loss after 20 Insults (Aged)[a] | % Color Loss after 20 Insults (Re-Aged)[d] |
|---|---|---|---|
| Base Formulation[b] | 24 | — | — |
| Example 5 | 19 | — | — |
| Example 6 | — | 14 | 10 |
| Example 6 (Duplicate Sample) | 10 | 8 | — |
| Example 7 | 11 | 10 | — |
| Comparative Example 2 | 22 | 22 | — |
| Industry Standard[c] | 10 | 11 | — |

[a]A sample of the same material as originally tested but with three month aging at ambient temperature (about 25 deg C.).
[b]Formulation containing all components listed in Table 3 except "Alkoxysilyl Functional Silicone".
[c]A commercially available material known for excellent color retention. The brand name cannot be disclosed here, because of certain legal obligations.
[d]A sample of the same material as originally tested but with eleven month aging at ambient temperature (about 25 deg C.).

The preceding specific embodiments and examples are illustrative of the overall invention, and the following claims should not be limited to such, unless specifically indicated.

What is claimed is:

1. A thermodynamically stable material comprising:
   (A) a cross-linked siloxane comprising:
      alkoxysilyl functionality, $-X-SiR^4_n(OR^5)_{3-n}$, and
      cross-links, $-E^1-Y-E^2-$, with each end of such cross-links bonded to a silicon,
   wherein,
      X is a divalent group that is a hydrocarbon, a siloxane or some combination of these,
      $R^4$ and $R^5$ are independently monovalent hydrocarbon groups,
      $E^1$ and $E^2$ are independently $-CH_2CH_2$ or $-CH=CH-$,
      Y is a divalent group that is a hydrocarbon, a siloxane or some combination of these and
      n is 0 to 2; and
   (B) a diluent.

2. The material of claim 1 wherein:
   (A) is a cross-liked siloxane comprising:
      alkoxysilyl functionality, $-X-SiR^4_n(OR^5)_{3-n}$, and
      cross-links, $-E^1-Y-E^2-$, with each end of such cross-links bonded to a silicon,
      wherein,
         X is a divalent hydrocarbon group having from 2 to 12 carbons,
         $R^4$ and $R^5$ are independently monovalent hydrocarbon groups having from 1 to 30 carbons,
         $E^1$ and $E^2$ are $-CH_2CH_2-$,
         Y is a divalent hydrocarbon group having from 1 to 30 carbons or a siloxane and
         n is 0 to 2.

3. The material of claim 1 wherein:
   (A) is a cross-linked alkoxysilyl functional siloxane of average formula:

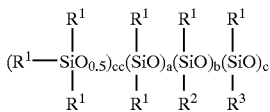

where,
$R^1$ is a monovalent hydrocarbon group;
$R^2$ is $-(CH_2)_d SiR^4_n(OR^5)_{3-n}$;
$R^3$ is $-E^1-Y-E^2-R^9$ or a siloxane containing $-E^1-Y-E^2-R^9$ with $E^1$ in this last mentioned siloxane bonded to silicon as well as to Y,
$R^4$ and $R^5$ are independently monovalent hydrocarbon groups;
$E^1$ and $E^2$ are independently $-CH_2CH_2-$ or $-CH=CH-$;
Y is a divalent group that is a hydrocarbon, a siloxane or some combination of these;
$R^9$ is

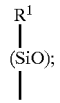

a is 0–100,000,000;
b is 1–50,000,000;
c is 1–10,000,000;
$4 \leq cc \leq 2c+2$;
d is 2–12;
n is 0–2.

4. The material of claim 3 where, in (A):
   $R^1$ is a monovalent hydrocarbon group having 1 to 12 carbons,
   $R^3$ is $-E^1-Y-E^2-R^9$,
   $R^4$ is a monovalent hydrocarbon group having 1 to 12 carbons,
   $R^5$ is methyl, ethyl, isopropyl, phenyl or benzyl,
   $E^1$ and $E^2$ are $-CH_2CH_2$, and
   Y is a divalent hydrocarbon group having from 1 to 30 carbons; and
   (B) is a siloxane other than that chosen for (A) or a mixture of siloxanes not containing that chosen for (A).

5. The material of claim 3 where the weight ratio of (A):(B) is from 1:100 to 10:1.

6. The material of claim 3 where in (A),
   $R^3$ is $-E^1-Y-E^2-R^9$,
   Y is

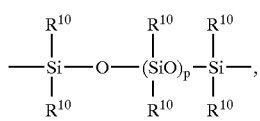

$R^{10}$ is a monovalent hydrocarbon group and
p is 0 to 20,000.

7. The material of claim 6 where in (A):
   $R^1$ is methyl,
   $R^4$ and $R^5$ are independently monovalent hydrocarbon groups having from 1 to 30 carbons,
   $E^1$ and $E^2$ are $-CH_2CH_2-$ and
   $R^{10}$ is methyl.

8. The material of claim 1 wherein
(A) is a cross-linked alkoxysilyl functional siloxane of average formula:

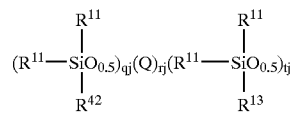

where,
$R^{11}$ is a monovalent hydrocarbon group;
$R^{42}$ is a monovalent hydrocarbon group or $-(CH_2)_d SiR^4_n(OR^5)_{3-n}$, with the proviso that $R^{42}$ is at least in part $-(CH_2)_d SiR^4_n(OR^5)_{3-n}$;
$R^{13}$ is $-E^1-R^{16}-Y-R^{17}-E^2-R^{19}$, or a siloxane containing $-E^1-R^{16}-Y-R^{17}-E^2-R^{19}$ with $E^1$ as this last mentioned siloxane bonded to silicon and $R^{16}$;
Q is on average at least 80 mole percent ($SiO_2$) with the balance made up of one or more other types of siloxane units;
$R^4$ and $R^5$ are independently monovalent hydrocarbon groups;
$E^1$ and $E^2$ are independently $-CH_2CH_2-$ or $-CH=CH-$;
$R^{16}$ and $R^{17}$ are independently divalent hydrocarbon groups or nullities;
Y is a divalent group that is a hydrocarbon, a siloxane or a combination of these
$R^{19}$ is

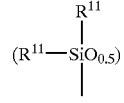

j is 1 to 100;
q is 1 to 500,000;
r is 1 to 1,000,000;
t is 1 to 100,000;
d is 2 to 12; and
n is 0 to 2, with the proviso that
q+t:r is 0.5 to 4.0.

9. The material of claim 8 where in (A):
   $R^{11}$ is a monovalent hydrocarbon group having from 1 to 40 carbons;
   $R^{13}$ is $-E^1-R^{16}-Y-R^{17}-E^2-R^{19}$;
   $R^4$ and $R^5$ are independently monovalent hydrocarbon groups having from 1 to 30 carbons;
   $R^{16}$ and $R^{17}$ are independently divalent hydrocarbons groups having from 1 to 8 carbons or a nullity;
   Y is

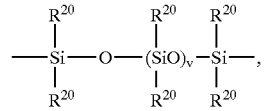

$R^{20}$ is a monovalent hydrocarbon group having from 1 to 40 carbons; and
v is 0 to 20,000.

10. The material of claim 1 wherein:
(A) is a cross-linked alkoxysilyl functional siloxane comprising subunits of formula:

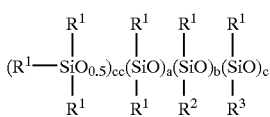

where, $R^1$ is a monovalent hydrocarbon group;

$R^2$ is $-(CH_2)_d SiR^4_n(OR^5)_{3-n}$;

$R^3$ is $-E^1-Y-E^2-R^9$ or a siloxane containing $-E^1-Y-E^2-R^9$ with $E^1$ in this last mentioned siloxane bonded to silicon as well as to Y, $R^4$ and $R^5$ are independently monovalent hydrocarbon groups;

$E^1$ and $E^2$ are independently $-CH_2CH_2-$ or $-CH=CH-$;

Y is a divalent group that is a hydrocarbon, a siloxane or some combination of these;

$R^9$ is

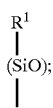

a is 0–1,000;

b is 1–500;

c is 1–100;

$4 <= cc <= 2c+2$;

d is 2–12;

n is 0–2.

11. The material of claim 1 wherein (A) is a cross-linked alkoxysilyl functional siloxane comprising subunits of formula:

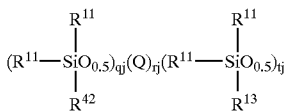

where, $R^{11}$ is a monovalent hydrocarbon group;

$R^{42}$ is a monovalent hydrocarbon group or $-(CH_2)_d SiR^4_n(OR^5)_{3-n}$, with the proviso that $R^{42}$ is at least in part $-(CH_2)_d SiR^4_n(OR^5)_{3-n}$;

$R^{13}$ is $-E^1-R^{16}-Y-R^{17}-E^2-R^{19}$ or a siloxane containing $-E^1-R^{16}-Y-R^{17}-E^2-R^{19}$ with $E^1$ in this last mentioned siloxane bonded to silicon and $R^{16}$;

Q is on average at least 80 mole percent $(SiO_2)$ with the balance made up of one or more other types of siloxane units;

$R^4$ and $R^5$ are independently monovalent hydrocarbon groups;

$E^1$ and $E^2$ are independently $-CH_2CH_2-$ or $-CH=CH-$;

$R^{16}$ and $R^{17}$ are independently divalent hydrocarbon groups or nullities;

Y is a divalent group that is a hydrocarbon, a siloxane or a combination of these $R^{19}$ is

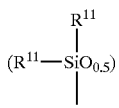

j is 1 to 100;

q is 1 to 500;

r is 1 to 1000;

t is 1 to 100;

d is 2 to 12; and n is 0 to 2, with the proviso that q+t:r is 0.5 to 4.0.

12. A method of making a thermodynamically stable material, the method comprising cross-linking, in the presence of a hydrosilylation catalyst, (1) an $\equiv$SiH functional siloxane and, (2) an alpha, omega diene, diyne or ene-yne, with the provisos that at least one of (1) and (2) has alkoxysilyl functionality, $-X-SiR^4_n(OR^5)_{3-n}$, where, X is a divalent group that is a hydrocarbon a siloxane or some combination of these, $R^4$ and $R^5$ are independently monovalent hydrocarbon groups and n is 0 to 2, that (1) and (2) are dispersed in a diluent, and that the weight ratio of (1)+(2)+ the product of the cross-linking of (1) and (2):diluent is 1:100 to 10:1.

13. The method of clam 12 wherein (1) is an $\equiv$SiH functional siloxane having alkoxysilyl functionality of the form, $-X-SiR^4_n(OR^5)_{3-n}$, where, X is a divalent group that is a hydrocarbon, a siloxane or some combination of these, $R^4$ and $R^5$ are independently monovalent hydrocarbon groups and n is 0 to 2.

14. The method of claim 13 where, (1) is an alkoxysilyl functional siloxane of average formula:

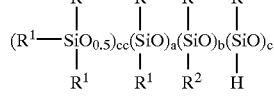

where, $R^1$ is a monovalent hydrocarbon group;

$R^2$ is $-(CH_2)_d SiR^4_n(OR^5)_{3-n}$;

$R^4$ and $R^5$ are independently monovalent hydrocarbon groups;

a is 0–1,000;

b is 1–500;

c is 1–100;

$2 <= cc <= 2c+2$;

d is 2–12; and n is 0–2;

(2) is $E^3-Y-E^4$ or a siloxane containing $E^3-Y-E^4$, where $E^3$ and $E^4$ are independently $CH_2=CH-$ or $CH\equiv C-$; and Y is a multivalent group that is a hydrocarbon, a siloxane or some combination of these.

15. The method of claim 13, wherein,
(1) is on average

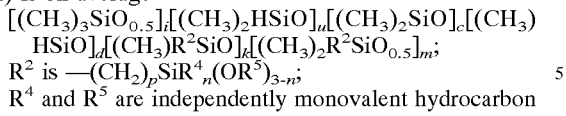

R² is —(CH₂)$_p$SiR⁴$_n$(OR⁵)$_{3-n}$;
R⁴ and R⁵ are independently monovalent hydrocarbon groups;
i is 0 to 2;
u is 0 to 2;
i+u+m=2;
c is 0 to 20,000;
d is 0 to 2000;
u+d>=2;
k is 0 to 2000;
m is 0 to 2;
k+m>=1;
p is 2 to 12;
n is 0 to 2; and
(2) is on average

e is 0 to 2;
f is 0 to 2;
e+f=2;
g is 0 to 20,000;
h is 0 to 1000; and
e+h>=2.

16. The method of claim 13, wherein,
(1) is on average

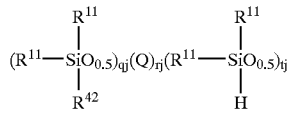

where,
R¹¹ is a monovalent hydrocarbon group;
R⁴² is a monovalent hydrocarbon group or —(CH₂)$_d$SiR⁴$_n$(OR⁵)$_{3-n}$, with the proviso that R⁴² is at least in part —(CH₂)$_d$SiR⁴$_n$(OR⁵)$_{3-n}$;
Q is on average at least 80 mole percent (SiO₂) with the balance made up of one or more other types of siloxane units;
R⁴ and R⁵ are independently monovalent hydrocarbon groups;
j is 1 to 100;

q is 1 to 500;
r is 1 to 1000;
t is 1 to 100;
d is 2 to 12;
n is 0 to 2;
q+t:r is 0.5 to 4; and
(2) is on average

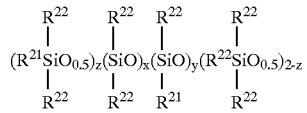

where x is 0 to 20,000,
y is 0 to 2000,
z is 0 to 2,
2<32 z+y<=2000,
R²¹ is a monovalent terminally aliphatic unsaturated hydrocarbon having from two to twelve carbons, and
R²² is a monovalent hydrocarbon having one to forty carbons.

17. The method of claim 12, wherein
(1) is an ≡Si—H functional polyorganosiloxane and
(2) is a polyorganosiloxane resin having alpha-omega diene or diyne or ene-yne functionality.

18. The method of claim 17 wherein at least 80 mole percent of subunits in the polyorganosiloxane resin of (2) are (SiO₂) and ((R$^i$)₃SiO$_{0.5}$), where R$^i$ is a monovalent hydrocarbon group, the ratio in (2) of siloxane units other than SiO₂ to SiO₂ units there is 0.5 to 4.0, and X in the alkoxysilyl functionality is a hydrocarbon.

19. The product of the method of claim 14.
20. The product of the method of claim 15.
21. The product of the method of claim 16.
22. The product of the method of claim 18.
23. A material, comprising the composition of claim 1, that is a personal care product.
24. The material of claim 23 that is a hair, skin or underarm care product.
25. The material of claim 24 that is a conditioner, moisturizer, body wash, cosmetic foundation, blush, lipstick, eye liner, mascara, eye shadow, antiperspirant or deodorant.

* * * * *